(12) United States Patent
Alster et al.

(10) Patent No.: US 10,034,887 B2
(45) Date of Patent: Jul. 31, 2018

(54) COMPOSITIONS AND METHODS FOR THE TREATMENT OF MEIBOMIAN GLAND DYSFUNCTION

(71) Applicant: M.G. Therapeutics, Ltd., Tel Aviv (IL)

(72) Inventors: Yair Alster, Tel Aviv (IL); Omer Rafaeli, Udim (IL); K. Angela MacFarlane, Menlo Park, CA (US); Cary Reich, Santa Barbara, CA (US); Shimon Amselem, Rehovot (IL); Doron Friedman, Carme-Yosef (IL)

(73) Assignee: M.G. THERAPEUTICS, LTD., Tel Aviv (IL)

( * ) Notice: Subject to any disclaimer, the term of this patent is extended or adjusted under 35 U.S.C. 154(b) by 0 days.

(21) Appl. No.: 15/269,833

(22) Filed: Sep. 19, 2016

(65) Prior Publication Data

US 2017/0035785 A1 Feb. 9, 2017

Related U.S. Application Data

(63) Continuation of application No. 14/732,622, filed on Jun. 5, 2015, now Pat. No. 9,463,201.

(60) Provisional application No. 62/065,716, filed on Oct. 19, 2014.

(51) Int. Cl.
| | | |
|---|---|---|
| *A61K 9/00* | (2006.01) | |
| *A61K 31/60* | (2006.01) | |
| *A61K 33/04* | (2006.01) | |
| *A61K 31/327* | (2006.01) | |
| *A61K 8/23* | (2006.01) | |

(52) U.S. Cl.
CPC ............ *A61K 31/60* (2013.01); *A61K 8/23* (2013.01); *A61K 9/0048* (2013.01); *A61K 31/327* (2013.01); *A61K 33/04* (2013.01); *A61K 9/0014* (2013.01)

(58) Field of Classification Search
CPC .................................................. A61K 9/0048
See application file for complete search history.

(56) References Cited

U.S. PATENT DOCUMENTS

| | | | |
|---|---|---|---|
| 3,236,730 A | 2/1966 | Galin | |
| 6,348,508 B1 | 2/2002 | Denick, Jr. et al. | |
| 7,288,259 B2 | 10/2007 | Sanders et al. | |
| 8,420,699 B1 | 4/2013 | Dubow | |
| 8,449,928 B2 | 5/2013 | Gilbard et al. | |
| 8,455,016 B2 | 6/2013 | Maskin | |
| 2004/0171561 A1* | 9/2004 | Popp ................... | A61K 9/0014 514/36 |
| 2004/0192647 A1 | 9/2004 | Babizhayev | |
| 2005/0197614 A1 | 9/2005 | Pritchard et al. | |
| 2006/0188471 A1 | 8/2006 | Podolsky et al. | |
| 2007/0166402 A1 | 7/2007 | Friedlaender et al. | |
| 2007/0269537 A1* | 11/2007 | Gupta ................... | A61K 8/0212 424/740 |
| 2008/0103376 A1 | 5/2008 | Felder | |
| 2009/0238810 A1 | 9/2009 | Nyunt | |
| 2010/0034870 A1 | 2/2010 | Sim et al. | |
| 2010/0204317 A1* | 8/2010 | Hunt ................... | A61K 31/341 514/473 |
| 2010/0256552 A1 | 10/2010 | Korb et al. | |
| 2010/0285155 A1 | 11/2010 | Gilbard et al. | |
| 2011/0022010 A1 | 1/2011 | Grenon et al. | |
| 2011/0059925 A1 | 3/2011 | Donnenfeld | |
| 2011/0104206 A1 | 5/2011 | Nanduri et al. | |
| 2011/0124725 A1 | 5/2011 | Maskin | |
| 2011/0130729 A1 | 6/2011 | Korb et al. | |
| 2011/0137214 A1 | 6/2011 | Korb et al. | |
| 2011/0294897 A1 | 12/2011 | Aberg et al. | |
| 2012/0016275 A1 | 1/2012 | Korb et al. | |
| 2012/0028929 A1 | 2/2012 | Power et al. | |
| 2012/0093876 A1 | 4/2012 | Ousler, III et al. | |
| 2012/0128763 A1 | 5/2012 | Maskin | |
| 2012/0190661 A1 | 7/2012 | Trogden et al. | |
| 2012/0226156 A1 | 9/2012 | Grenon et al. | |
| 2012/0264681 A1 | 10/2012 | Braiman-Wiksman et al. | |
| 2012/0288575 A1 | 11/2012 | Gilbard et al. | |
| 2013/0053733 A1 | 2/2013 | Korb et al. | |
| 2013/0131171 A1 | 5/2013 | Maskin | |
| 2013/0184242 A1 | 7/2013 | Eini et al. | |
| 2013/0224272 A1 | 8/2013 | Gao et al. | |

(Continued)

FOREIGN PATENT DOCUMENTS

| | | |
|---|---|---|
| CN | 101612161 A | 12/2009 |
| EP | 0930072 A1 | 7/1999 |

(Continued)

OTHER PUBLICATIONS

Akyol-Salman et al. Efficacy of topical N-acetylcysteine in the treatment of meibomian gland dysfunction. J Ocul Pharmacol Ther 26(4):329-333 (2010).

Barrault et al. Immortalized sebocytes can spontaneously differentiate into a sebaceous-like phenotype when cultured as a 3D epithelium. Exp Dermatol 21:299-319 (2012).

Chew et al. An instrument for quantifying meibomian lipid on the lid margin: the Meibometer. Curr Eye Res 12(3):247-254 (1993).

Co-pending U.S. Appl. No. 15/279,301, filed Sep. 28, 2016.

Heiligenhaus et al. Therapy of dry eye disorders [Therapie von Benetzungsstorungen]. Klin Monatsbl Augenheilkd 204:162-168 (1994).

(Continued)

*Primary Examiner* — Benjamin Packard
(74) *Attorney, Agent, or Firm* — Wilson, Sonsini, Goodrich & Rosati

(57) ABSTRACT

Described herein are compositions and methods for the treatment of meibomian gland dysfunction. Said compositions and methods comprise keratolytic agents, such as salicylic acid, selenium disulfide, or the like. Topical administration of said compositions to the eyelid margin or surrounding areas provides therapeutic benefit to patients suffering from meibomian gland dysfunction.

27 Claims, No Drawings

(56) References Cited

U.S. PATENT DOCUMENTS

| | | |
|---|---|---|
| 2013/0274214 A1 | 10/2013 | Brubaker |
| 2013/0280340 A1 | 10/2013 | Dobbie |
| 2013/0281390 A1 | 10/2013 | Brubaker |
| 2013/0331768 A1 | 12/2013 | Nichamin |
| 2013/0344128 A1 | 12/2013 | Gao et al. |
| 2013/0345185 A1 | 12/2013 | Mitra et al. |
| 2014/0005171 A1 | 1/2014 | Aukunuru et al. |
| 2014/0058340 A1 | 2/2014 | Guillon et al. |
| 2014/0142055 A1 | 5/2014 | Hosseini et al. |
| 2014/0142668 A1 | 5/2014 | Guillon et al. |
| 2014/0154333 A1 | 6/2014 | Moloney |
| 2015/0265565 A1 | 9/2015 | O'Haimhirgin |
| 2016/0106775 A1 | 4/2016 | Alster et al. |

FOREIGN PATENT DOCUMENTS

| | | |
|---|---|---|
| EP | 1621191 A1 | 2/2006 |
| EP | 2633852 A1 | 9/2013 |
| WO | WO-9611686 A1 | 4/1996 |
| WO | WO-9724116 A2 | 7/1997 |
| WO | WO-03050190 A2 | 6/2003 |
| WO | WO-2007070463 A2 | 6/2007 |
| WO | WO-2010006117 A2 | 1/2010 |
| WO | WO-2012092320 A2 | 7/2012 |
| WO | WO-2012161112 A1 | 11/2012 |
| WO | WO-2013003731 A2 | 1/2013 |
| WO | WO-2015017316 A2 | 2/2015 |
| WO | WO-2015169728 A1 | 11/2015 |
| WO | WO-2017055924 A2 | 4/2017 |

OTHER PUBLICATIONS

Knop et al. The International Workshop on Meibomian Gland Dysfunction: Report of the Subcommittee on Anatomy, Physiology, and Pathophysiology of the Meibomian Gland. IOVS 52(4):1938-1978 (2011).

Koenig et al. Organic Sulfur Derivatives. V.2 Preparation and Properties of Some Long-Chain Mercapto Acids and Related Compounds. J Org Chem 23:1525-1530 (1958).

Qiao et al. Emerging treatment options for meibomian gland dysfunction. Clinical Ophthalmology 7:1797-1803 (2013).

PCT/IB2015/02164 International Search Report and Written Opinion dated Mar. 29, 2016.

U.S. Appl. No. 14/732,622 Office Action dated Nov. 19, 2015.

Nederfors et al. Effects of the antihypertensive drug captopril on human salivary secretion rate and composition. Eur J Oral Sci 103(6):351-354 (Dec. 1995) (Abstract).

Nichols. The International Workshop on Meibomian Gland Dysfunction: Introduction. Invest Ophthalmol Vis Sci 52(4):1917-1921 (2011).

Seifert et al. Immunocytochemical and ultrastructure evaluation of the distribution of nervous tissue and neuropeptides in meibomian gland. Graefe's Arch Clin Exp Ophthalmol 234:648-656 (1996).

U.S. Appl. No. 15/279,301 Office Action dated Mar. 29, 2017.

Nederfors et al. Effects of the antihypertensive drug captopril on human salivary secretion rate and composition. EurJ Oral Sci 103(6):351-354 (Dec. 1995) (Abstract).

Butovich et al. Human tear film and meibum. Very long chain wax esters and (O-acyl)-omega-hydroxy fatty acids of meibum. J Lipid Res 50(12):2471-2485 (2009).

PCT/IB2015/02164 International Preliminary Report on Patentability dated May 4, 2017.

PCT/US2016/01510 International Search Report and Written Opinion dated May 24, 2017.

U.S. Appl. No. 15/279,301 Office Action dated Aug. 31, 2017.

Millar et al. The effect of dietary and pharmacological manipulation of lipid production in the Meibomian and Harderian glands of the rabbit. Lacrimal Gland, Tear Film, and Dry Eye Syndromes 3. Advances in Experimental Medicine and Biology 506:431-440 (2002).

Nagymihalyi et al. The influence of eyelid temperature on the delivery of Meibomian oil. Exp Eye Res 78:367-370 (2004).

U.S. Appl. No. 15/279,301 Office Action dated Mar. 14, 2018.

* cited by examiner

COMPOSITIONS AND METHODS FOR THE TREATMENT OF MEIBOMIAN GLAND DYSFUNCTION

CROSS REFERENCE

This application is a continuation application of U.S. patent application Ser. No. 14/732,622, filed Jun. 5, 2015; and claims the benefit of U.S. Provisional Application No. 62/065,716, filed Oct. 19, 2014, all of which are incorporated by reference herein in their entireties.

BACKGROUND OF THE INVENTION

Meibomian gland dysfunction, or MGD, is a leading contributor of dry eye syndrome and is often characterized by a keratinized obstruction of the terminal duct of the meibomian gland.

SUMMARY OF THE INVENTION

Prior to the methods and formulations described herein, there were no pharmacological agents useful for the treatment of MGD, including for the removal of the keratinized obstruction of the meibomian gland, or for the prevention of further keratinized obstruction of the meibomian gland. Current technology for removing keratinized obstruction of the meibomian gland is limited to physical removal methods, some of which are quite painful to the patient.

As such, described herein, are methods and formulations for treating MGD. In one embodiment is provided a method for treating meibomian gland dysfunction in a patient in need thereof, comprising topically administering to the patient a composition that reaches the eyelid margin of the patient, wherein the composition comprises a therapeutically-effective amount of at least one keratolytic agent in an ophthalmically-acceptable carrier. In some embodiments, the keratolytic agent is benzoyl peroxide, coal tar, dithranol, salicylic acid, selenium disulfide, alpha-hydroxy acid, urea, lactic acid, sodium thioglycolate, zinc pyrithione, or zinc L-pyrrolidone carboxylate. In some embodiments, the keratolytic agent is salicylic acid or selenium disulfide. In some embodiments, the keratolytic agent is selenium disulfide. In some embodiments, the concentration of the selenium disulfide in the composition is between about 0.1% to about 10%. In some embodiments, the keratolytic agent is salicylic acid. In some embodiments, the composition is topically administered to the patient until the keratinized obstruction is relieved. In some embodiments, the composition is topically administered to the patient periodically after reliving the keratinized obstruction. In some embodiments, the topical administration is a single administration. In some embodiments, the topical administration is a periodic administration. In some embodiments, the periodic administration is once a day. In some embodiments, periodic administration is two times a day. In some embodiments, the composition for topical administration is a semi-solid. In some embodiments, the composition for topical administration is homogenous. In some embodiments, the composition for topical administration is a dispersion. In some embodiments, the composition for topical administration is hydrophilic. In some embodiments, the composition for topical administration has an oleaginous base. In some embodiments, the ophthalmically-acceptable carrier comprises at least one ophthalmically-acceptable excipient. In some embodiments, the administration of the composition results in enhanced meibum production.

In one embodiment is provided a method for treating meibomian gland dysfunction in a patient in need thereof, comprising topically administering to the patient a composition that reaches the eyelid margin of the patient, wherein the composition consists of a therapeutically-effective amount of a keratolytic agent in an ophthalmically-acceptable carrier. In some embodiments, the keratolytic agent is salicylic acid or selenium disulfide. In some embodiments, the keratolytic agent is selenium disulfide. In some embodiments, the concentration of the selenium disulfide in the composition is between about 0.1% to about 10%. In some embodiments, the administration of the composition results in enhanced meibum production. In some embodiments, the composition for topical administration is homogenous. In some embodiments, the composition for topical administration is a dispersion. In some embodiments, the composition for topical administration is hydrophilic. In some embodiments, the composition for topical administration has an oleaginous base. In some embodiments, the ophthalmically-acceptable carrier comprises at least one ophthalmically-acceptable excipient.

In one embodiment are methods for treating MGD by administering a meibomian gland opening pharmacological agent which allows for the opening of the meibomian gland (at least in part), the passage of the keratinized obstruction (at least in part), and/or the prevention of subsequent keratin obstructions (at least to the extent that such obstructions lead to meibomian gland dysfunction) within the meibomian gland. In one embodiment, the formulation comprises a therapeutically-effective amount of the meibomian gland opening pharmacological agent. In one further or alternative embodiment, the formulation comprises an additional therapeutic agent that is not a meibomian gland opening pharmacological agent. In one further or alternative embodiment, the formulation comprises an additional meibomian gland opening pharmacological agent. In one alternative embodiment, the formulation does not include any additional therapeutic agents other than an additional meibomian gland opening pharmacological agent. In one alternative embodiment, the formulation consists only of a single meibomian gland opening pharmacological agent and no other therapeutic agents. In any of the aforementioned embodiments, the formulation optionally comprises an ophthalmically-acceptable carrier. In one further embodiment, the ophthalmically-acceptable carrier comprises an ophthalmically-acceptable excipient.

In one aspect, the methods and formulations described herein include pharmacological agents that are useful for the treatment of MGD in a subject in need. In some embodiments, the formulations described herein are applied to the eyelid margin of a patient in need. In some embodiments, multiple applications of the formulations are required.

In some embodiments, the eye is shielded, at least in part, to prevent the pharmacological agents from contacting the eye of the subject in need. Further described are kits comprising a formulation described herein along with a device that shields the eye from contact with the formulation.

The methods and formulations described herein include an active agent at a therapeutic level, that by itself, or in combination with other components, acts to open (at least in part) an obstructed meibomiam gland or prevent (at least in part) further obstruction of the meibomian gland. Further, such active agent is formulated or applied, such that it is acceptable to the surface of the eye (i.e. not causing undue irritation or disruption to the epithelial surface of the eye), and without compromising lipid producing cells in contact with the formulation.

In some embodiments, the formulation is applied for a duration and frequency that is acceptable and practical to the physician or patient administering the agent. For example, a physician applies a formulation described herein weekly or twice a week for several weeks to induce opening (at least in part) of the obstruction and the patient applies a different formulation on a daily basis, or the patient uses a more potent formulation on a daily basis for several weeks and then, subsequently uses a less potent formulation of a daily basis thereafter.

In some embodiments the method of application varies, depending on the concentration of the active agent and/or the severity of the MGD to be treated, including but not limited to shielding the ocular surface. In other embodiments, the method of application or formulation, is varied to enhance the penetration or residency time on the target tissue to enhance the treatment effect. In other embodiments, the method of application or formulation, is varied to enhance the penetration or residency time on the target tissue to minimize the amount of time necessary. In other embodiments, the method of application or formulation, is formulated (e.g., viscosity enhancement and/or skin-adhesiveness) to increase contact with the target tissue while minimizing contact with non-target tissues, including the eye, and thus limit or reduce any undesired collateral activity.

In certain aspects of the methods and formulations described herein, the concentration of the active agent, and the components of co-formulation are optimized to deliver the minimum effective concentration of active agent to achieve the therapeutic benefit while minimizing any ocular irritation or disruption, or irritation or disruption to surrounding ocular tissues. The method and formulation described herein are means for removal (at least in part) of the keratinized obstruction of the meibomian gland, or to prevent further keratinized obstruction (at least in part) of the meibomian gland.

The formulations include at least one meibomian gland opening pharmacological agent. In some embodiments the meibomian gland opening pharmacological agent is a keratolytic and/or keratoplastic agent. In some embodiments the keratolytic and/or keratoplastic agent within the formulation is the active agent responsible for opening or maintaining the patency of the meibomian gland canal.

In some embodiments agents having primarily keratolytic effect are used. In some embodiments agents having primarily keratoplastic effect are used. In some embodiments agents having both keratolytic and keratoplastic effect are used. In some embodiments the keratolytic and/or keratoplastic agent enhances lipid production in the meibomian glands. In some embodiments the meibomian gland opening pharmacological agent is an anesthetic. In some embodiments the meibomian gland opening pharmacological agent is an anti-inflammatory agent. In some embodiments the meibomian gland opening pharmacological agent is an antioxidant agent. In some embodiments the meibomian gland opening pharmacological agent is an inhibitor of prostaglandin synthethase. In some embodiments the meibomian gland opening pharmacological agent is a lipooxygenase or cyclooxygenase enzyme.

In one aspect described herein are methods for treating meibomian gland dysfunction in a patient in need thereof comprising topically administering to at least the non-mucosal epithelial side of the eyelid margin of the patient a composition comprising a therapeutically-effective amount of at least one meibomian gland obstruction opening pharmacological agent applied in an ophthalmically-acceptable manner or formulation. In one aspect of the methods and formulation described herein, the formulation includes a pharmaceutical excipient.

In some embodiments, the meibomian gland opening pharmacological agent is a keratolytic and/or keratoplastic agent chosen from benzoyl peroxide, coal tar, dithranol, salicylic acid, selenium disulfide, inorganic selenium compounds such as selenium disulfide, $SeCl_4$, $Na_2SeO_3$, organoselenium compounds such as Ebselen (2-phenyl-1,2-benzisoselenazol-3(2H)-one) or its analogues, alpha-hydroxy acid, urea, lactic acid or sodium thioglycolate. In some embodiments, the keratolytic and/or keratoplastic agent is chosen from benzoyl peroxide, coal tar, dithranol, salicylic acid or selenium disulfide. In some embodiments, the keratolytic and/or keratoplastic agent is salicylic acid or selenium disulfide. In some embodiments, the keratolytic and/or keratoplastic agent is salicylic acid. In some embodiments, the keratolytic and/or keratoplastic agent is selenium disulfide. In some embodiments, the at least one keratolytic and/or keratoplastic agent is salicylic acid. In some embodiments, the at least one keratolytic and/or keratoplastic agent is selenium disulfide. In some embodiments, the salicylic acid is present from about 0.1% to about 30%. In some embodiments the selenium disulfide is present from about 0.1% to about 10%.

In some embodiments, the meibomian gland opening pharmacological agent is an anesthetic chosen from an aminoamide local anesthetic and/or an aminoester local anesthetic. In one embodiment, the aminoamide local anesthetic or the aminoester local anesthetic is present at a concentration between about 4% and about 80%. In one embodiment, the aminoamide local anesthetic or the aminoester local anesthetic is present at a concentration between about 6% and about 60%. In one embodiment, the aminoamide local anesthetic or the aminoester local anesthetic is present at a concentration between about 8% and about 50%. In one embodiment, the aminoamide local anesthetic or the aminoester local anesthetic is present at a concentration between about 10% and about 40%. In one embodiment, the aminoamide local anesthetic or the aminoester local anesthetic is present at a concentration between about 12% and about 45%. In one embodiment, the aminoamide local anesthetic or the aminoester local anesthetic is present at a concentration between about 14% and about 40%. In one embodiment, the formulation comprises more than one local anesthetic.

In some embodiments, topical administration of the composition comprising at least one meibomian gland opening pharmacological agent occurs twice a week. In some embodiments, topical administration of the composition comprising at least one meibomian gland opening pharmacological agent occurs every other day. In some embodiments, topical administration of the composition comprising at least one meibomian gland opening pharmacological agent occurs every day. In some embodiments, topical administration of the composition comprising at least one meibomian gland opening pharmacological agent occurs several times a day.

In some embodiments, the composition for topical administration is a liquid or a semi-solid. In some embodiments, the composition for topical administration is an emulsion semi-solid. In some embodiments, the composition for topical administration is a cream. In some embodiments, the composition for topical administration is an ointment. In some embodiments, meibomian gland opening pharmacological agent is suspended within the composition. In some embodiments, the composition for topical administration is a lotion. In some embodiments, the composition for topical administration is a gel.

DETAILED DESCRIPTION OF THE INVENTION

Prior to the methods and formulations described herein, there were no pharmacological agents useful for the treatment of MGD, including for the removal of the keratinized obstruction of the meibomian gland, or to prevention of further keratinized obstruction of the meibomian gland.

Current technology for removing keratinized obstruction of the meibomian gland is limited to painful physical removal methods. As such, described herein, are methods for treating MGD by administering a meibomian gland opening pharmacological agent which allows the passage of the keratinized obstruction, and also preventing the buildup of subsequent keratin obstructions within the meibomian gland. The meibomian gland opening pharmacological agents described herein include agents for acute therapies, for use, e.g., by a physician or other trained specialist, and agents for chronic therapies, e.g., either by a physician or other trained specialist, or by the patient. Certain meibomian gland opening pharmacological agents are provided herein; further provided herein are methods and assays for identifying further meibomian gland opening pharmacological agents (e.g., by testing the relative keratolytic activity of a potential agent, such as examples 1 and 2).

Meibomian Gland

The meibomian glands are large sebaceous glands located in the eyelids, and unlike skin, are unassociated with hair. The meibomian glands produce the lipid layer of the tear film that protects it against evaporation of the aqueous phase. The meibomian gland orifice is located on the epithelial side of the lid margin, and is only a few hundred microns from the mucosal side. The glands are located on both upper and lower eyelids, with higher amounts of the glands on the upper eyelid. A single meibomian gland is composed of clusters of secretory acini that are arranged circularly around a long central duct and connected to it by short ductules. The terminal part of the central duct is lined by an ingrowth of the epidermis that covers the free lid margin and forms a short excretory duct that opens as an orifice at the posterior part of the lid margin just anterior to the mucocutaneous junction near the inner lid border. The oily secretion composed of lipids is synthesized within the secretory acini. The lipid secretion is a liquid at near body temperature and is delivered to the skin of the lid margin as a clear fluid, called "meibum." It forms shallow reservoirs on the upper and lower lid margins, and consists of a complex mixture of cholesterol, wax, cholesteryl esters, phospholipids, with small amounts of triglycerides, triacylglycerols, and hydrocarbons. The separate meibomian glands are arranged in parallel, and in a single row throughout the length of the tarsal plates in the upper and lower lids. The extent of the glands corresponds roughly to the dimensions of the tarsal plates.

The term "keratinized obstruction" as used herein refers to a blockage of the meibomian gland, regardless of the location of the blockage. In some embodiments, the blockage is complete, whereas in other embodiments, the blockage is partial. Regardless of the degree of blockage, such keratinized obstruction leads to meibomian gland dysfunction. In some embodiments, the keratinized obstruction is composed of keratinized material and lipids. In some embodiments, the keratinized obstruction is a blockage at the meibomian gland orifice and excretory duct. In some embodiments, the keratinized obstruction is caused by keratinization of the epithelium at the lid margin and meibomian gland. In certain instances, the keratin obstruction is influenced by the migration or aberrant differentiation of stem cells. In some embodiments, the keratinized obstruction results in reduced delivery of oil to the lid margin and tear film, and stasis inside the meibomian gland that causes increased pressure, resultant dilation, acinar atrophy, and low secretion. In certain instances, keratinization of the meibomian gland causes degenerative gland dilation and atrophy.

Meibomian Gland Dysfunction (MGD)

The term, "meibomian gland dysfunction," as used herein, refers to chronic, diffuse abnormality of the meibomian glands, that is characterized by terminal duct obstruction or qualitative or quantitative changes in the glandular secretion, or both. MGD may result in alteration of the tear film, eye irritation symptoms, inflammation, or ocular surface disease. The most prominent aspects of MGD are obstruction of the meibomian gland orifices and terminal ducts and changes in the meibomian gland secretions.

MGD is a leading contributor of dry eye syndrome. The occurrence of dry eye syndrome is widespread and affects about 20 million patients in the United States alone. Dry eye syndrome is a disorder of the ocular surface resulting from either inadequate tear production or excessive evaporation of moisture from the surface of the eye. Tears are important to corneal health because the cornea does not contain blood vessels, and relies on tears to supply oxygen and nutrients. Tears and the tear film are composed of lipids, water, and mucus, and disruption of any of these can cause dry eye. An inadequate amount of lipids flowing from the meibomian glands as caused by a keratinized obstruction, may cause excessive evaporation, thereby causing dry eye syndrome.

MGD is not synonymous with posterior blepharitis, which describes inflammatory conditions of the posterior lid margin. MGD may cause posterior blepharitis, but MGD may not always be associated with inflammation or posterior blepharitis. MGD also refers to functional abnormalities of the meibomian gland, while "meibomian gland disease," describes a broad range of meibomian gland disorders, that includes neoplasia and congenital disease. Clinical signs of MGD include meibomian gland dropout, altered meibomian gland secretion, and changes in lid morphology.

In some embodiments, altered meibomian gland secretion is detected by physically expressing the meibomian glands by applying digital pressure to the tarsal plates. In subjects without MGD, the meibum is a pool of clear oil. In MGD, both the quality and expressibility of the expressed material is altered. The altered meibum is also known as meibomian excreta and is made up of a mixture of altered secretions and keratinized epithelial material. In MGD, the quality of expressed lipid varies in appearance from a clear fluid, to a viscous fluid containing particulate matter and densely opaque, toothpaste-like material. The meibomian orifices may exhibit elevations above surface level of the lid, which is referred to as plugging or pouting, and is due to obstruction of the terminal ducts and extrusion of a mixture of meibomian lipid and keratinized material.

Obstructive MGD is characterized by all or some of the following: 1) chronic ocular discomfort, 2) anatomic abnormalities around the meibomian gland orifice (which is one or more of the following: vascular engorgement, anterior or posterior displacement of the mucocutaneous junction, irregularity of the lid margin) and 3) obstruction of the meibomian glands (obstructive findings of the gland orifices by slit lamp biomicroscopy (pouting, plugging or ridge), decreased meibum expression by moderate digital pressure).

Current methods for assessing and monitoring MGD symptoms include, but are not limited to patient questionnaires, meibomian gland expression, tear stability break up time, and determining the number of patent glands as seen by digital expression.

In some embodiments, the symptoms of a patient are assessed by asking the patient a series of questions. Questionnaires allow the assessment of a range of symptoms associated with ocular discomfort. In some embodiments, the questionnaire is the SPEED questionnaire. The SPEED questionnaire assesses frequency and severity of a patient's dry eye symptoms. It examines the occurrence of symptoms on the current day, past 72 hours and past three months. A SPEED score is tallied based on the patient's answers to the questions, to give a range of severity of the patient's symptoms. The SPEED questionnaire includes questions such as the following: 1) what dry eye symptoms are you experiencing, and when do they occur? 2) how frequently do you experience dryness, grittiness, or scratchiness in your eyes? 3) how often do you experience soreness or irritation of the eyes? 4) how often do you experience burning or watering of the eyes? 5) how often do you experience eye fatigue? and 6) how severe are the symptoms?

Meibomian gland expressibility is optionally determined to assess the meibomian gland function. In normal patients, meibum is a clear to light yellow oil. Meibum is excreted from the glands when digital pressure is placed on the glands. Changes in meibomian gland expressibility are one potential indicator of MGD. In some embodiments, during expression, quantifying the amount of physical force applied during expression is monitored in addition to assessing lipid volume and lipid quantity.

Tear stability break up time (TBUT) is a surrogate marker for tear stability. Tear film instability is a core mechanism in dry eye and MGD. Low TBUT implies a possibility of lipid layer compromise and MGD. TBUT is optionally measured by examining fluorescein breakup time, as defined as the time to initial breakup of the tear film after a blink. Fluorescein is optionally applied by wetting a commercially available fluorescein-impregnated strip with saline, and applied to the inferior fornix or bulbar conjuctiva. The patient is then asked to blink several times and move the eyes. The break up is then analyzed with a slit lamp, a cobalt blue filter, and a beam width of 4 mm. The patient is instructed to blink, and the time from upstroke of the last blink to the first tear film break or dry spot formation is recorded as a measurement.

Other methods for assessing MGD symptoms, include but are not limited to, Schirmer test, ocular surface staining, lid morphology analysis, meibography, meibometry, interferometry, evaporimetry, tear lipid composition analysis, fluorophotometry, meiscometry, osmolarity analysis, indices of tear film dynamics, evaporation and tear turnover.

Current treatments for MGD include lid warming, lid massage, lid hygiene, lid expression and meibomian gland probing. Pharmacological methods, prior to those described herein, have not been used.

Lid hygiene is considered the primary treatment for MGD and consists of three components: 1) application of heat, 2) mechanical massage of eyelids and 3) cleansing the eyelid. Eyelid warming procedures improve meibomian gland secretion by melting the pathologically altered meibomian lipids. Warming is achieved by warm compresses or devices. Mechanical lid hygiene includes the use of scrubs, mechanical expression and cleansing with various solutions of the eyelashes and lid margins. Lid margins are optionally also cleansed with hypoallergenic bar soap, dilute infant shampoo or commercial lid scrubs. Physical expression of meibomian glands is performed in a physician's office or is performed by the patient at home. The technique varies from gentle massage of the lids against the eyeball to forceful squeezing of the lids either against each other or between a rigid object on the inner lid surface and a finger, thumb, or rigid object (such as a glass rod, Q-tip, or metal paddle) on the outer lid surface. The rigid object on the inner lid surface protects the eyeball from forces transferred through the eyelid during expression and to offer a stable resistance, to increase the amount of force that is applied to the glands.

Eyelid warming is limited because the warming melts the lipids, but does not address movement of the keratinized material. Further, eyelid warming induces transient visual degradation due to corneal distortion. Mechanical lid hygiene is also limited because the force needed to remove an obstruction can be significant, resulting in significant pain to the patient. The effectiveness of mechanical lid hygiene is limited by the patient's ability to tolerate the associated pain during the procedure. Other treatments for MGD are limited.

Physical opening of meibomian glands obstruction by meibomian gland expression is an acceptable method to improve meibomian gland secretion and dry eye symptoms. In addition probing of the meibomian gland canal has been used to open the obstructed canal. Both methods, expression and probing, are limited, however, by the pain induced by the procedure, the possible physical insult to the gland and canal structures and their short lived effect estimated at days and weeks. Therefore, methods are needed to improve patient comfort, which will not cause harm to the meibomian glands and canals, that will reduce the dependency on frequent office visits and improve secretion of meibum.

Meibomian Gland Opening Pharmacological Agents

Keratolytic and/or Keratoplastic Agents

The keratolytic and keratoplastic agents described herein are useful in either as an acute therapy (e.g., by a trained specialist or physician) or as a chronic therapy (e.g., in the hands of a patient, or alternatively, by a trained specialist or physician). The agents are tested, in certain embodiments, using the assays and methods described herein (e.g., as described in the examples).

One embodiment provides a method for treating MGD in a patient in need thereof comprising topical administration of a composition comprising a meibomian gland opening pharmacological agent, wherein the meibomian gland opening pharmacological agent is a keratolytic agent or keratoplastic agent. In some embodiments, the meibomian gland opening pharmacological agent is a keratolytic agent chosen from allantoin, benzoyl peroxide, inorganic selenium compounds such as selenium disulfide, $SeCl_4$, $Na_2SeO_3$, organoselenium compounds such as Ebselen (2-phenyl-1, 2-benzisoselenazol-3(2H)-one) or its analogues, coal tar, dithranol, salicylic acid, selenium disulfide, alpha-hydroxy acid, urea, lactic acid, sodium thioglycolate, zinc pyrithione, or zinc L-pyrrolodione carboxylate. In some embodiments the keratolytic agent is not retinoic acid.

It is important that the agents used to open the meibomian gland have minimal undesired side effects, such a gland atrophy and/or interference with lipid production in the gland. Thus, in some embodiments agents with such undesired side effects are not included within the scope of the formulations described herein. By way of example, retinoic acid, or a retinoic acid derivative may cause gland atrophy or interfere with lipid production in certain patients or at certain concentrations or frequency of use, and as such, in some embodiments retinoic acid, or a retinoic acid derivative are not used in the formulations and methods described herein.

In certain embodiments, a mild or weak keratolytic and/or keratoplastic agents is used in the methods and formulations described herein, e.g., with subjects that produce low levels of keratin. Such mild or weak keratolytic and/or keratoplastic agents are optionally used in a maintenance therapy setting. Mild or weak keratolytic and/or keratoplastic agents include lower concentrations of active keratolytic and/or keratoplastic agents, as well as keratolytic and/or keratoplastic agents that have low inherent activity (as determined, e.g., by the methods described herein). In certain embodiments, the mild or weak keratolytic and/or keratoplastic agents is not boric acid.

One embodiment provides a method for treating meibomian gland dysfunction in a patient in need thereof, comprising topically administering to the patient a composition that reaches the eyelid margin of the patient, wherein the composition comprises a therapeutically-effective amount of at least one keratolytic agent in an ophthalmically-acceptable carrier. In one embodiment, the keratolytic agent is benzoyl peroxide. In another embodiment, the keratolytic agent is coal tar. In another embodiment, the keratolytic agent is dithranol. In another embodiment, the keratolytic agent is salicylic acid. In another embodiment, the keratolytic agent is selenium disulfide. In another embodiment, the keratolytic agent is selenium sulfide. As used herein, the terms "selenium sulfide" and "selenium disulfide" are used interchangably to refer to the chemical compound having the formula $SeS_2$ where the ratio of selenium to sulfur is approximately 1:2. In another embodiment, the keratolytic agent is zinc pyrithione. In another embodiment, the keratolytic agent is zinc L-pyrrolidone carboxylate.

In some embodiments, more than one keratolytic agent is used.

In some embodiments, administration of a keratolytic agent to a keratin obstruction results in proteolysis of desmosomes forming tight junctions between keratinocytes. In some embodiments, administration of a keratolytic agent results in lysis, including the hydrolysis of disulfide bonds. In some embodiments, administration of a keratolytic agent reduces the production of keratin One embodiment provides a method for treating MGD in a patient in need thereof by administering a topical composition comprising a keratolytic agent, wherein the keraloytic agent comprises benzoyl peroxide. In some embodiments, the composition comprises 2.5%, 5%, or 10% benzoyl peroxide. In some embodiments, the composition comprising benzoyl peroxide is a suspension, emulsion, cream, lotion, gel, or ointment. In some embodiments, the composition comprising benzoyl peroxide is applied as a thin layer to clean skin initially once daily on alternate days, and is then gradually increased up to twice daily as tolerance develops.

One embodiment provides a method for treating MGD in a patient in need thereof by administering a topical composition comprising a keratolytic agent, wherein the keratolytic agent is coal tar. In some embodiments, the composition comprises a 5% to 10% solution of coal tar. In some embodiments, the composition comprising coal tar is at least 5%, 6%, 7%, 8%, 9%, 10% or greater solution of coal tar. In one embodiment, the composition comprising coal tar is a 1% ointment of crude coal tar. In some embodiments, the coal tar inhibits excessive proliferation of epidermal cells by reducing DNA synthesis and mitotic activity to normal levels.

One embodiment provides a method for treating MGD in a patient in need thereof by administering a topical composition comprising a keratolytic agent, wherein the keratolytic agent is dithranol. In some embodiments, the composition comprises a 0.1% to 2.0% ointment of dithranol. In some embodiments, the composition comprising dithranol is at least 0.1, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0, or greater of dithranol. In some embodiments, the composition comprising dithranol is started as a 0.1% ointment. After 7 days, the concentration may be increased to 0.25% and subsequently doubled, if necessary, at weekly intervals to a maximum strength of 2%. In some embodiments, a thin layer of ointment is applied once daily to the affected areas for 2-4 weeks. In some embodiments, the ointment is left in place for 10 to 20 minutes before the area is rinsed thoroughly. In some embodiments, the dithranol slows epidermal cell division and inhibits excessive proliferation and keratinization of epidermal cells in patients.

One embodiment provides a method for treating MGD in a patient in need thereof by administering a topical composition comprising a keratolytic agent, wherein the keratolytic agent is salicylic acid. In some embodiments, the composition comprises 0.1% to 6% salicylic acid. In some embodiments, the composition comprises at least 0.1%, 1%, 2%, 3%, 4%, 5%, 6% or greater salicylic acid. In some embodiments, the composition comprising salicylic acid is an ointment or paste. In some embodiments, the composition comprising salicylic acid is applied initially as a thin layer of 2% ointment or paste, and is applied daily. In some embodiments, the concentration is gradually increased to a maximum of 5%, and treatment is continued for as long as necessary.

One embodiment provides a method for treating MGD in a patient in need thereof by administering a topical composition comprising a keratolytic agent, wherein the keratolytic agent is selenium disulfide. In some embodiments, the composition comprises 0.1% to 10% selenium disulfide. In some embodiments, the composition comprises at least 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, or greater selenium disulfide. In some embodiments, the composition comprising selenium disulfide is a semi-solid. In some embodiments, the composition comprising selenium disulfide is a lotion. In some embodiments, the composition comprising selenium disulfide is a cream. In some embodiments, the composition comprising selenium disulfide is an ointment. In some embodiments, the composition comprising selenium disulfide is a suspension. In some embodiments, the composition comprising selenium disulfide is a solution. In some embodiments the composition containing selenium disulfide enhances lipid production from the meibomian glands.

In some embodiments, the composition comprises inorganic selenium compounds that are inhibitors of prostaglandin synthase, the enzyme involved in the production of prostaglandins. The selenium compounds demonstrating this inhibitory effect include $SeCl_4$ and $Na_2SeO_3$. It is known that the proinflammatory action of prostaglandins enhances keratinization and therefore these water-soluble inorganic selenium compounds that interfere with the production of prostaglandin may be useful in reducing keratinization.

In some embodiments, the composition comprises organo-selenium compounds. Organo-selenium compounds such as Ebselen are antioxidant and anti-inflammatory agents inhibiting cyclooxygenase and lipooxygenase enzymes and acting as scavenger of hydrogen peroxide as well as hydroperoxides including membrane bound phospholipid and cholesterylester hydroperoxides. Antiinflammatory agents are known to inhibit keratinization and therefore ebselen and other organo-selenium analogues may act as keratolytic agents through this antioxidant/anti-inflammatory activity.

In some embodiments, the formulation comprising the keratolytic and/or keratoplastic agent further includes an additional therapeutic agent that is not a meibomian gland opening pharmacological agent. In some embodiments the formulation does not contain jojoba wax or jojoba extract. In some embodiments the formulation does not include boric acid. In some embodiments, the formulation does not include retinoic acid. Alternatively, in some embodiments, the formulation with the keratolytic and/or keratoplastic agent excludes any additional therapeutic agent, other than an optional additional meibomian gland opening pharmacological agent.

Local Anesthetics

One embodiment provides a method for treating MGD in a patient in need thereof comprising topical administration of a composition comprising a meibomian gland opening pharmacological agent, wherein the meibomian gland opening pharmacological agent is a local anesthetic. In some embodiments, the meibomian gland opening pharmacological agent is a local anesthetic chosen from an aminoamide local anesthetic, or an aminoester local anesthetic.

The term "local anesthetic" as used herein refers to an agent that induces a reversible absence of pain sensation. In some embodiments, a local anesthetic may also induce temporary muscle paralysis in addition to inducing a reversible absence of pain sensation.

The local anesthetic agents described herein are useful primarily as an acute therapy, e.g., under the guidance of a physician or other trained specialist. The agents are tested, in certain embodiments, using the assays and methods described herein (e.g., as described in the examples).

In some embodiments, the local anesthetic is an aminoamide. In some embodiments, the local anesthetic is an aminoester. In some embodiments, the local anesthetic comprises a combination of two or more local anesthetics. In some embodiments, the combination comprises an aminoamide local anesthetic and an aminoester local anesthetic.

In some embodiments, the local anesthetic is an aminoester selected from the group consisting of: benzocaine, chloroprocaine, cocaine, cyclomethycaine, dimethocaine, larocaine, piperocaine, propoxycaine, procaine, novocaine, proparacaine, tetracaine, and amethocaine.

In some embodiments, the local anesthetic is an aminoamide selected from the group consisting of: articaine, bupivacaine, cinchocaine, dibucaine, etidocaine, levobupivacaine, lidocaine, lignocaine, mepivacaine, prilocaine, ropivacaine, trimecaine.

In some embodiments, the local anesthetic is a combination of lidocaine and prilocaine or a combination of lidocaine and tetracaine.

In some embodiments, the local anesthetic is a naturally derived local anesthetic. In some embodiments, the naturally derived local anesthetic is selected from the group consisting of: saxitoxin, neosaxitoxin, tetrodotoxin, menthol, eugenol, and cocaine.

In some embodiments, the local anesthetic is mixed with a vasoconstrictor to increase the duration of the local anesthesia by constricting blood vessels. In some embodiments, priolocaine hydrochloride is mixed with epinephrine. In some embodiments, lidocaine, bupivacaine are mixed with epinephrine. In some embodiments, iontocaine is mixed with lidocaine and epinephrine. In some embodiments, septocaine is mixed with a combination of articaine and epinephrine. In some embodiments, local anesthetic, bupivacaine or lidocaine are mixed in combination with a steroid.

Pharmaceutical Excipient

In other embodiments, the topical compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier). Exemplary excipients are described, for example, in *Remington: The Science and Practice of Pharmacy* (Gennaro, 21$^{st}$ Ed. Mack Pub. Co., Easton, Pa. (2005)).

Methods of Treatment Utilizing Meibomian Gland Opening Pharmacological Agents

Described herein are methods for treating MGD in a patient in need comprising topical administration of a meibomian gland opening pharmacological agent to the eyelid margin of the patient in need. There are two potential categories of administration. One occurs with the assistance of a health-care provider: this category includes both acute and maintenance uses of the meibomian gland opening pharmacological agent. An acute use, in one embodiment, requires a stronger meibomian gland opening pharmacological agent (either in terms of concentration of the agent or the inherent activity of the agent). A maintenance use, in one embodiment, allows for the use of lower concentrations of the agent, or agents with lower inherent activity. A maintenance use, in one embodiment, involves a patient at a routine visit to the health care provider. Both acute uses and maintenance uses optionally involve use of an eye-protecting device or apparatus. In one embodiment, the acute use is performed by the health care provider, and the maintenance use is performed by the patient or non-health care provider. The second potential category of administration does not occur with the active assistance of a health care provider, but rather involves the patient applying the meibomian gland opening pharmacological agent to his/her eyelid margin. In one embodiment, such administration occurs over an extended period of time; one way of describing this patient-administered multi-administration mode is as a chronic use. In general, different or second formulations of the meibomian gland opening pharmacological agent are recommended for chronic or patient-administered uses. In one embodiment the different or second formulation utilizes a lower concentration of the meibomian gland opening pharmacological agent. In another embodiment, the second or different formulation utilizes a meibomian gland opening pharmacological agent that has a lower activity than the first formulation.

It should be understood that the present methods also include the physical removal of the obstruction in the meibomian gland, followed by chronic and/or maintenance administration of the meibomian gland opening pharmacological agent described herein.

One embodiment provides a method for treating meibomian gland dysfunction in a patient in need thereof, comprising topically administering to the patient a composition that reaches the eyelid margin of the patient, wherein the composition comprises a therapeutically-effective amount of at least one keratolytic agent in an ophthalmically-acceptable carrier. In some embodiments, the topical administration of the composition comprising a therapeutically-effective amount of at least one keratolytic agent in an ophthalmically-acceptable carrier results in enhanced meibum production.

In some embodiments, the topical administration of the composition comprising a therapeutically-effective amount of at least one keratolytic agent in an ophthalmically-acceptable carrier occurs until the keratinized obstruction is relieved. In some embodiments, the topical administration of the composition comprising a therapeutically-effective amount of at least one keratolytic agent in an ophthalmically-acceptable carrier occurs periodically after relieving of the keratinized obstruction. In some embodiments, the topical administration of the composition comprising a therapeutically-effective amount of at least one keratolytic agent in an ophthalmically-acceptable carrier is a single administration. In some embodiments, the topical administration of the composition comprising a therapeutically-effective amount of at least one keratolytic agent in an ophthalmically-acceptable carrier is a periodic administration. In some embodiments, the topical administration of the composition comprising a therapeutically-effective amount of at least one keratolytic agent in an ophthalmically-acceptable carrier occurs once a day. In some embodiments, the topical administration of the composition comprising a therapeutically-effective amount of at least one keratolytic agent in an ophthalmically-acceptable carrier occurs twice a day.

In some embodiments, the composition for topical administration, comprising a therapeutically-effective amount of at least one keratolytic agent in an ophthalmically-acceptable carrier is a semi-solid. In some embodiments, the composition for topical administration, comprising a therapeutically-effective amount of at least one keratolytic agent in an ophthalmically-acceptable carrier is homogenous. In some embodiments, the composition for topical administration, comprising a therapeutically-effective amount of at least one keratolytic agent in an ophthalmically-acceptable carrier is a dispersion. In some embodiments, the composition for topical administration, comprising a therapeutically-effective amount of at least one keratolytic agent in an ophthalmically-acceptable carrier is hydrophilic. In some embodiments, the composition for topical administration, comprising a therapeutically-effective amount of at least one keratolytic agent in an ophthalmically-acceptable carrier has an oleaginous base. In some embodiments, the composition for topical administration, comprising a therapeutically-effective amount of at least one keratolytic agent in an ophthalmically-acceptable carrier has at least one ophthalmically-acceptable excipient.

One embodiment provides a method for treating MGD in a patient in need thereof comprising topical administration of a composition comprising a meibomian gland opening pharmacological agent. In some embodiments, the topical administration of the composition comprising a meibomian gland opening pharmacological agent occurs once a week. In some embodiments, the topical administration of the composition comprising a meibomian gland opening pharmacological agent occurs twice a week. In some embodiments, the topical administration of the composition comprising a meibomian gland opening pharmacological agent occurs every other day. In some embodiments, the topical administration of the composition comprising a meibomian gland opening pharmacological agent occurs every day. In some embodiments, the topical administration of the composition comprising a meibomian gland opening pharmacological agent occurs several times a day.

In some embodiment, the method comprises treatment in an acute treatment scenario. In another embodiment, the method comprises treatment of a patient naïve to treatment. In another embodiment, the method comprises treatment in a chronic treatment scenario. In another embodiment, the method comprises treatment in a maintenance therapy scenario. In an acute treatment scenario, the administered dosage of meibomian gland opening pharmacological agent maybe higher than the administered dosage of meibomian gland opening pharmacological agent employed in a chronic treatment scenario or a maintenance therapy scenario. In an acute treatment scenario, the meibomian gland opening pharmacological agent maybe different from the meibomian gland opening pharmacological agent employed in a chronic treatment scenario. In some embodiments, the course of therapy begins in the initial phase of therapy as an acute treatment scenario and later transitions into a chronic treatment scenario or a maintenance therapy scenario. In some embodiments, the meibomian gland opening pharmacological agent administered in the acute treatment scenario is a local anesthetic, and the meibomian gland opening pharmacological agent administered in the chronic treatment scenario or a maintenance therapy scenario is a keratolytic agent and/or keratoplastic agent. In some embodiments, the meibomian gland opening pharmacological agent administered in the acute treatment scenario is a keratolytic agent and/or keratoplastic agent, and the meibomian gland opening pharmacological agent administered in the chronic treatment scenario or a maintenance therapy scenario is a keratolytic agent and/or keratoplastic agent.

In certain clinical presentations, patients may require an initial treatment administered by a physician or healthcare professional, to initially open the blockage of the meibomiam gland, either by placing a more highly concentrated formulation of one of the therapeutic agents described herein. In the event the higher concentration formulations are required, the application thereof may require ocular shielding or other activity to minimize the impact of irritation or disruption of the ocular surface or surrounding tissues. Following such a procedure, a patient may be given a different formulation of active agent to take home to apply periodically to the lid margin to maintain the patency of the meibomiam gland. Such application may occur twice daily, once a day, weekly or monthly, depending on the formulation activity and the desired product profile of the therapy.

One aspect of the methods of treatment described herein is the location of the topical administration of the composition. In one embodiment, the composition comprising a meibomian gland opening pharmacological agent is administered such that no irritation to eye occurs. In one embodiment, the composition comprising a meibomian gland opening pharmacological agent is administered to the eye lid margin.

One additional embodiments of the methods of treatment described herein is the use of a protective element provided to the eye to avoid irritation to the eye. Although the formulations described herein are generally non-irritating, in some embodiments (e.g., high concentration of agent or when used on a sensitive eye) a protective element provides an additional layer of safety and comfort for the patient. In one embodiment, the composition comprising a meibomian gland opening pharmacological agent is administered while an eye shield is placed on the eye to reduce contact of the pharmacological agent with the cornea and/or conjunctiva such that reduced irritation to eye occurs. In some embodiments, the eye shield is a contact lens or an eye covering. In some embodiments, the eye covering comprises a self-adhesive. In one embodiment, the composition comprising a meibomian gland opening pharmacological agent is administered while the lid is pulled away from the globe to reduce contact of the pharmacological agent with the cornea and/or conjunctiva such that reduced irritation to eye occurs.

Certain Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The terms "treat," "treating," or "treatment" as used herein, include reducing, alleviating, abating, ameliorating, relieving, or lessening the symptoms associated with MGD in either a chronic or acute therapeutic scenario. In one embodiment, treatment includes a reduction of a terminal duct obstruction.

The term "recurrence," or "reducing relapse" refers to return of MGD symptoms in a chronic therapeutic scenario.

The term "opening" refers to the clearing (at least in part) of an obstructed meibomian gland canal or orifice and/or maintaining the patency of the meibomian gland canal or orifice.

The term "keratolytic agent" and/or "keratoplastic agent" as used herein refers to an agent that softens, disrupts, dissolves, solubilizes, or loosens a keratinized obstruction, or prevents the formation of a keratinized obstruction. Specifically, the term "Keratolytic agents" refers to agents used to promote softening and dissolution of keratin and the term "keratoplastic agents" refers to agents used to reduce keratin production.

The term "lotion" describes an emulsion liquid dosage form. This dosage form is generally for external application to the skin (US FDA Drug Nomenclature Monograph, number C-DRG-00201).

The term "cream" describes an emulsion semisolid dosage form, usually containing >20% water and volatiles and/or <50% hydrocarbons, waxes or polyols as the vehicle. A cream is more viscous than a lotion. This dosage form is generally for external application to the skin (US FDA Drug Nomenclature Monograph, number C-DRG-00201).

The term "ointment" describes a semisolid dosage form, usually containing <20% water and volatiles and/or >50% hydrocarbons, waxes or polyols as the vehicle. This dosage form is generally for external application to the skin or mucous membranes (US FDA Drug Nomenclature Monograph, number C-DRG-00201).

The term "solution" describes a clear, homogeneous liquid dosage form that contains one or more chemical substances dissolved in a solvent or mixture of mutually miscible solvents (US FDA Drug Nomenclature Monograph, number C-DRG-00201).

The term "suspension" refers to a heterogeneous mixture containing solid particles that are sufficiently large for sedimentation.

EXAMPLES

Example 1: Assessing Keratolytic Efficacy of Salicylic Acid, Benozyl Peroxide, and Retinoic Acid Keratolytic efficacy of an agent is optionally assessed by examining stratum corneum (SC) tape strippings to measure the total SC protein amount removed and on the tape. The amount of skin mass on the tape is directly proportional to the amount of keratolysis.

Salicylic acid is a keratolytic, while retinoic acid is known mostly for its comedolytic properties, and benzoyl peroxide is known mostly for its anti-microbial mechanism. Here, all three were examined for relative keratolytic efficacy.

The tape stripping results revealed that benzoyl peroxide has keratolytic effects comparable to that of salicylic acid and retinoic acid. After 3 hours, benzoyl peroxide was significantly more effective in interfering with SC cohesion than either salicylic acid or retinoic acid under the present conditions. After 6 hours of treatment, all three were similarly effective. The SC removal by retinoic acid increased by approximately 35% for 3-6 hours, as compared to about 10% for salicylic acid and benzoyl peroxide. Hence, retinoic acid's keratolytic properties after prolonged application were comparable to benzoyl peroxide.

Example 2: Effect of Selenium Disulfide and Salicylic Acid on Keratin Removal in Forearm and Eyelid The objective of the study was to evaluate the effect of potential keratolytic agents on keratin removal as detected by lissamine green removal. Lissamine green stains keratin.

The following reagents were used for the study: 1% salicylic acid (SA), 2.5% selenium disulfide (SD), diluted 1:10 selenium disulfide (SD/10), soap containing citric acid salicylic acid (SK), tearless shampoo (SS), and lissamine green (LG).

Study #1: Forearm A

LG stains keratin and was therefore used to evaluate the effectiveness of various agents on their ability to remove five keratin spots (2.5 cm×2.5 cm) of LG. LG was applied to each forearm of both arms of 2 subjects. Each spot was compared to the contralateral spot in the contralateral forearm. Different substances were administered over the LG spot.

The following comparison spots were analyzed: SA vs. control; SA vs. SK; SA vs. SD; SD vs. control; SD vs. SK.

Ten minutes following application, gentle scrubbing (×10) was administered to each spot using a golf club spud in order to evaluate the LG removal. Lissamine color intensity was compared between each pair to evaluate the degree of LG removal (better removal=less LG remnant was defined as superior).

The results were identical in both subject and superiority in removal of keratin. SA>control; SA<SK; SA<SD; SD>control; SD roughly equal to SK.

Study #2: Forearm B

Three spots (2.5 cm×2.5 cm) of lissamine green (LG) application were done in each forearm of one subject. Each spot was compared to the contralateral spots in the contralateral forearm. Different substances were administered over the LG spot. The following comparisons were analyzed: SS vs. SK; SD vs. SD/10.

Ten minutes following application, gentle scrubbing (×10) was administered to each spot using a golf club spud in order to evaluate the degree of LG removal.

The results were as follows: SS<SK; SD>SD/10

Study #3: Forearm C

Four spots (2.5 cm×2.5 cm) of lissamine green (LG) application were applied to the forearm of one subject. SK was applied for: 10 minutes, 5 minutes, 3 minutes, 2 minutes, and 1 minute.

At the end of each period, a gold club was used to scrape (×10) the material.

After 10 and 5 minute application, the SK almost completely removed the keratin. The three minute application of SK resulted in good removal of keratin. The two minute application of SK was suboptimal in removing keratin. The 1 minute application was unsatisfactory in removing keratin.

Study #4: Eyelid A

The goal of this study was to investigate the tolerability of SD applied to the eye of a subject. A light layer of SD was applied to the lower lid in one subject. The application of SD resulted in immediate severe irritation. The eye was washed immediately. Irritation and red eye persisted for about 30 minutes and then subsided.

Study #5: Eyelid B

LG was applied to the lower eyelid of one subject. Because SD is irritating to the eye, safety precautions were taken. The anterior surface of the eye was protected by placing a contact lens over cornea followed by anesthesia drops and pulling of the eyelid away from the globe while SD was present on the eyelid. SD was applied on the central part of the eye lid while the nasal and temporal parts were left only with the LG stain. Ten minutes following application, gentle scrubbing (×2) with a sponge tip was performed to the entire lower eyelid.

LG staining was completely removed in the central part that was treated with SD and was not removed in the temporal or nasal areas that were not treated. During the procedure some stinging was felt, but was tolerable to the subject. No adverse events occurred.

Study #6: Eyelid C

LG was applied to the lower lid. SD was applied on the nasal third of the lid, SD/10 was applied on the temporal third, and the middle third was left only with the LG stain. Ten minutes following application, gentle scrubbing (×2) with a sponge tip was performed to the lower eyelid.

The LG staining was completely removed in the nasal third that was treated with SD. LG staining was not removed in the central third that was not treated. LG staining was slightly removed to the temporal third that was treated with SD/10. The procedure was uneventful, slight burning was felt on nasal side (non-diluted SD), but not on the temporal side (diluted SD).

Conclusion of Studies 1-6.

The results demonstrated the following:

1) Selenium disulfide (2.5% preparation) is highly irritable to the eye and cannot be applied without substantial precaution to avoid mucosal and corneal touch and the use of topical anesthesia.

2) The presumed effectiveness scale was as followed (most effective to not effective): (SD=SK)>(SD/10)=(SA)>(SS)>(control).

3) Soap alone (the detergent) is not sufficient for removing the keratin.

4) Selenium disulfide and the SK soap were found to have the same effect on skin keratin removal. Note that the SK soap contains a couple of keratolytic agents (salicylic acid and possibly citric acid) with unknown concentrations.

5) The duration of SK application is important in determining its effect.

6) Selenium disulfide is highly effective in removing keratin from the eyelid.

7) The diluted 1:10 selenium disulfide was found to be significantly less effective in the forearm skin keratin removal compared to the non-diluted SD (2.5%).

8) The diluted 1:10 selenium disulfide was found to be less effective in the lid keratin removal compared to the non-diluted SD (2.5%) but better than control.

Example 3: 17 Day Study of Selenium Disulfide 2.5% Treatment Over Eyelid Margins in Patients with MGD A novel observation of use of selenium disulfide was also observed, giving rise to the novel hypothesis that at least one agent active agent is effective in pharmacologically treating the obstruction in the meibomian gland, without the need for additional mechanical intervention.

Eight patients with meibomian gland disease with signs and symptoms of dry eye, were treated in one of their eyes for 17 days, twice a week (5 total applications) with a commercially available suspension comprising 2.5% selenium disulfide. The suspension was placed over the treated eyelid margin for 5 minutes. The fellow eye was not treated and served as a control. After 5 treatment sessions in which 2.5% selenium disulfide suspension was applied to the eyelid margin, dry eye signs and symptoms improved significantly compared to the fellow control eyes. Results of the eight patients who underwent 2.5% selenium disulfide treatment are shown in Table 1.

TABLE 1

Assessment of MGD and dry eye symptoms in patients treated with a 2.5% selenium disulfide suspension for 17 days

| | Treated Eye | | | Control Eye (untreated) | | |
|---|---|---|---|---|---|---|
| Assessment | Baseline | Day 17 | pValue | Baseline | Day 17 | pValue |
| SPEED questionnaire | 12.00 | 7.88 | 0.01 | 11.88 | 9.38 | 0.11 |
| TBUT (sec.) | 7.38 | 16.81 | 0.004 | 10.91 | 12.00 | 0.65 |
| Number of open meibomian gland on digital expression | 2.75 | 6.25 | 0.02 | 3.63 | 3.13 | 0.71 |

Example 4: Effect of High Concentration Topical Anesthetic Cream (Lidocaine 23% and Tetracaine 7% Ointment) Treatment A study in which mechanical expression and probing was were compared was conducted. Since both methods are painful to the patient high dose topical anesthesia (Lidocaine 23% and Tetracaine 7% Ointment) not indicated for ocular use was applied of the lids prior to either procedures. The topical anesthesia was not removed from the eye following its application. A novel observation of an additional mechanism of anesthetic was also observed, giving rise to the novel hypothesis that at least one agent active agent is effective in pharmacologically treating the obstruction in the meibomian gland. In a certain set of cases, local anesthetic agent was observed to have a full therapeutic benefit in alleviating gland obstruction without the need for further mechanical intervention and separate from nominally providing comfort to assist in the mechanical extraction of gland content.

Two patients with MGD were treated topically to the lower lids of both eyes with a 23% lidocaine and 7% tetracaine cream applied 2-3 times. The cream was not removed from the eyelids. Probing was done to one eye, while expression was done to the fellow eye. Probing was successful in both patients. Expression was partially successful in one patient (expressible material came from about 50% of glands) and no expressible material came from the eye of the other patient (e.g. the glands were completely blocked). A few hours after the procedure, both patients presented with corneal abrasions that were likely caused by the anesthetic cream.

After 48 hours, both patients were examined again. The patient that had the complete blockage (patient #2) demonstrated dramatic (50%) improvement in his meibomian gland function (a combination of number of open glands and quality of meibum) (improvement of MG score from 96 to 52) with clear meibum present following light digital expression in many glands. The other patient (patient #1) showed about 25% improvement (score improved from 46 to 36). The results of patients 1 and 2 are shown in Table 2.

Nine other patients were treated using lidocaine 4% ophthalmic gel. In these cases where meibomian gland blockage was present, no improvement in meibomian gland function was observed.

TABLE 2

Treatment of patients 1 and 2 with 23% lidocaine and 7% tetracaine ointment followed by meibomian gland expression or probing.

| Patient Number | Gender | Age | Baseline Combined MG score* | 48 hours Post Treatment Combined MG score* |
|---|---|---|---|---|
| 1 | F | 71 | 48 | 36 |
| 2 | M | 63 | 96 | 42 |

*Each MG is assigned a number based on outcome of expression where 0 = clear meibum, 1 = whitish meibum, 2 = yellow thicker meibum, 3 = paste like meibum, and 4 = total obstruction. This number is multiplied by the number of glands observed. The higher the number, the more severe the obstruction.

Example 5: Effect of High Concentration Topical Anesthetic Cream (Lidocaine 23% and Tetracaine 7% Ointment) Treatment on Meibomian Gland Patency Four patients with MGD were treated with high dose topical anesthesia (Lidocaine 23% and Tetracaine 7% Ointment) not indicated for ocular use on the lower eyelid margins only. The eyelid was pulled away from the globe and was taped to the lower cheek for 15 minutes to avoid direct contact between the medication and the anterior surface of the eye. A contact lens was also placed as a barrier for the drug in case some leaks towards the globe High concentration topical anesthetic cream was applied as a thin layer and was wiped off after 15 minutes. The procedure did not cause any adverse events. The results are listed below in Table 3. In patient #6, significant meibomian gland function improvement was observed. A doubling of the tear meniscus height was measured using Oculus M5 Kertometer in the study eye and no change was observed in the fellow eye. In all other patients, no change in MG score of tear meniscus in either eye was observed. It is noted that while in example 5 the high concentration topical anesthesia was left on the lid and was not wiped off, in this group of patients it was wiped off after 15 minutes.

TABLE 3

Treatment of patients with Telica (23% lidocaine and 7% tetracaine ointment) and the effect on meibomian gland patency.

| Patient Number | Gender | Age | Tear meniscus | Combined MG score* | Baseline Tear meniscus (M5) | 48 hours Post Treatment Combined MG score* |
|---|---|---|---|---|---|---|
| 3 | M | 67 | 0.37 | 88 | 0.39 | 78 |
| 4 | F | 58 | 0.29 | 96 | 0.25 | 88 |
| 5 | F | 68 | 0.32 | 93 | 0.33 | 90 |
| 6 | F | 62 | 0.4 | 92 | 0.71 | 48 |

What is claimed is:

1. A method for treating meibomian gland dysfunction in a patient in need thereof, comprising topically administering to the patient a composition that reaches the eyelid margin of the patient, wherein the composition comprises a therapeutically-effective amount of at least one keratolytic agent in an ophthalmically-acceptable carrier, wherein the keratolytic agent is salicylic acid and wherein the meibomian gland dysfunction is characterized by keratinized obstruction.

2. The method of claim 1, wherein the concentration of the salicylic acid in the composition is between about 0.1% to about 30%.

3. The method of claim 1, wherein the concentration of the salicylic acid in the composition is between about 0.1% to about 10%.

4. The method of claim 1, wherein the concentration of the salicylic acid in the composition is between about 0.1% to about 6%.

5. The method of claim 1, wherein composition is topically administered to the patient until the keratinized obstruction is relieved.

6. The method of claim 1, wherein composition is topically administered to the patient periodically after relieving the keratinized obstruction.

7. The method of claim 1, wherein the topical administration is a single administration.

8. The method of claim 1, wherein the topical administration is a periodic administration.

9. The method of claim 8, wherein the periodic administration is once a day.

10. The method of claim 8, wherein the periodic administration is two times a day.

11. The method of claim 1, wherein the composition for topical administration is a semi-solid.

12. The method of claim 1, wherein the composition for topical administration is homogenous.

13. The method of claim 1, wherein the composition for topical administration is a dispersion.

14. The method of claim 1, wherein the composition for topical administration is hydrophilic.

15. The method of claim 1, wherein the composition for topical administration has an oleaginous base.

16. The method of claim 1, wherein the ophthalmically-acceptable carrier comprises at least one ophthalmically-acceptable excipient.

17. The method of claim 1, wherein the administration of the composition results in enhanced meibum production.

18. A method for treating meibomian gland dysfunction in a patient in need thereof, comprising topically administering to the patient a composition that reaches the eyelid margin of the patient, wherein the composition consists essentially of a therapeutically-effective amount of a keratolytic agent in an ophthalmically-acceptable carrier, wherein the keratolytic agent salicylic acid and wherein the meibomian gland dysfunction is characterized by keratinized obstruction.

19. The method of claim 18, wherein the concentration of the salicylic acid in the composition is between about 0.1% to about 30%.

20. The method of claim 18, wherein the concentration of the salicylic acid in the composition is between about 0.1% to about 10%.

21. The method of claim 18, wherein the concentration of the salicylic acid in the composition is between about 0.1% to about 6%.

22. The method of claim 18, wherein the administration of the composition results in enhanced meibum production.

23. The method of claim 18, wherein the composition for topical administration is homogenous.

24. The method of claim 18, wherein the composition for topical administration is a dispersion.

25. The method of claim 18, wherein the composition for topical administration is hydrophilic.

26. The method of claim 18, wherein the composition for topical administration has an oleaginous base.

27. The method of claim 18, wherein the ophthalmically-acceptable carrier comprises at least one ophthalmically-acceptable excipient.

* * * * *

UNITED STATES PATENT AND TRADEMARK OFFICE
CERTIFICATE OF CORRECTION

PATENT NO. : 10,034,887 B2
APPLICATION NO. : 15/269833
DATED : July 31, 2018
INVENTOR(S) : Yair Alster et al.

It is certified that error appears in the above-identified patent and that said Letters Patent is hereby corrected as shown below:

In the Claims

In Claim 18, Column 21, Lines 21-22 "wherein the keratolytic agent salicylic acid" should read -- wherein the keratolytic agent is salicylic acid --.

Signed and Sealed this
Twenty-sixth Day of February, 2019

Andrei Iancu
*Director of the United States Patent and Trademark Office*